(12) United States Patent
Mashima et al.

(10) Patent No.: US 7,642,357 B2
(45) Date of Patent: Jan. 5, 2010

(54) IRIDIUM COMPLEXES

(75) Inventors: Kazushi Mashima, Ikeda (JP); Tsuneaki Yamagata, Minoo (JP)

(73) Assignee: Takasago International Corporation, Tokyo (JP)

( * ) Notice: Subject to any disclaimer, the term of this patent is extended or adjusted under 35 U.S.C. 154(b) by 420 days.

(21) Appl. No.: 11/660,935

(22) PCT Filed: Aug. 27, 2004

(86) PCT No.: PCT/JP2004/012394

§ 371 (c)(1),
(2), (4) Date: Apr. 2, 2007

(87) PCT Pub. No.: WO2006/022020

PCT Pub. Date: Mar. 2, 2006

(65) Prior Publication Data

US 2009/0036696 A1 Feb. 5, 2009

(51) Int. Cl.
C07F 15/00 (2006.01)
B01J 31/00 (2006.01)
(52) U.S. Cl. .......................... 548/103; 556/23; 502/152
(58) Field of Classification Search ................... 556/23; 548/103; 502/152
See application file for complete search history.

(56) References Cited

U.S. PATENT DOCUMENTS 5,011,995 A 4/1991 Pugin et al.

FOREIGN PATENT DOCUMENTS

JP 64-47723 2/1989
JP 11-335334 12/1999

OTHER PUBLICATIONS

Crabtree et al., Organometallics, vol. 4, No. 3, pp. 519-523 (1985).*
Robert Crabtree, Accounts of Chemical Research, vol. 12, pp. 331-337 (1979).*
Jozsef Bakos et al., Rhodium(1)-Sulfonated-bdpp† Catalysed Asymmetric Hydrogenation of Imines in Aqueous-Organic Two-phase Solvent Systems, J.Chem. Soc., Chem. Commun., 1991, p. 1684-1685.

Deryn E. Fogg et al., A comparison of catalytic activity for imine hydrogenation using Ru ditertiary phosphine complexes, including chiral systems, Inorganica Chimia Acta, 1994, vol. 222, p. 85-90.
Felix Spindler et al., Novel Diphosphinoiridium Catalysts for the Enantioselective Hydrogenation of N-Arylketimines, Angew. Chem. Int. Ed. Engl., 1990, vol. 29, p. 558-559.
Kazuhide Tani et al., Iridium(I)-Catalyzed Asymmetric Hydrogenation of Prochiral Imines; Protic Amines as Catalyst Improvers, Chemistry Letters, 1995, p. 955-956.
Y. Ng Cheong Chan et al., Iridium (III) Hydride Complexes for the Catalytic Enantioselective Hydrogenation of Imines, J.Am. Chem. Soc., 1990, vol. 112, p. 9400-9401.
Romano Dorta, et al, Chiral Xyliphos Complexes for the Catalytic Imine Hydrogenation Leading to the Metolachlor Herbicide: Isolation of Catalyst-Substrate Adducts, Chem. Eur. J., 2004, vol. 10, p. 267-278.
Tsuneaki Yamagata, et al., Highly Stereoselective Synthesis and Structure of Hydride (carboxylato) iridium (III) Complexes and Their Application to the Catalytic Reaction, Proceedings of the 51$^{st}$ Annual Forum on complex Chemistry, 327(2a-A07) (Sep. 28 to 30, 2001) with English Translation.
Kazunori Hoshida, et al., Synthesis and structural characterization of hydrido(thilato)iridium(III) complexes, Proceedings I of the 81$^{st}$ Spring Meeting of Chem. Soc. Of Japan, 449 (1PB-059) (Mar. 26 to 29, 2002), with English Translation.
Tsuneaki Yamagata, et al, Highly Steroselective Synthesis and Structure of Hydrido(carboxylato)Ir(III) Complexes and Catalytic Asymmetric Hydrogenation of Imines, Proceedings of Molecular Chirality-2002, 47 (PS-3)(Jun. 6, 2002) with English Abstract.

* cited by examiner

*Primary Examiner*—Porfirio Nazario Gonzalez
(74) *Attorney, Agent, or Firm*—Wenderoth, Lind & Ponack, L.L.P.

(57) ABSTRACT

The present invention has as its object to provide an iridium complex represented by the general formula:

$$[(\text{I r H L}^1 \text{ L}^2)_2(\mu-X^1)(\mu-X^2)(\mu-X^3)]X^4 \qquad (1)$$

(wherein $L^1$ and $L^2$ may be the same or different and each represent a monodendate neutral ligand, or each cooperate with the other to form a bidendate neutral ligand; $X^1$, $X^2$ and $X^3$ may be the same or different, and each represent a halogen atom; and $X^4$ is a counter-anion). Also, the present invention provides a novel catalyst which can achieve excellent performance as a catalyst for asymmetric synthesis, especially asymmetric hydrogenation, in terms of chemical selectivity, enantioselectivity and catalytic activity, and the like.

12 Claims, No Drawings

IRIDIUM COMPLEXES

TECHNICAL FIELD

The present invention relates to iridium complexes and to catalysts intended for use in the asymmetric hydrogenation, which catalysts contain the same.

BACKGROUND ART

In synthesizing optically active amine compounds, heretofore, there have conventionally been employed, for example, the procedure which comprises the use of a naturally occurring amine compound and the method which involves synthesizing a racemic amine, followed by optical resolution with use of an optically active carboxylic acid, and the like. However, the former procedure encounters difficulties in obtaining or procuring the starting compounds, while the latter method has left unsolved the inconvenience that optical resolution fails to produce the desired compound in amounts in excess of those being present prior to such chemical resolution. In order to solve such problems, in recent years, extensively intensified investigation has been conducted into a method for synthesizing optically active amines through catalytic asymmetric hydrogenation of imines. For example, there have been known the methods in which a rhodium complex is used (for example, refer to J. Chem. Soc., Chem. Commun., 1991, pp. 1684), a ruthenium complex is utilized (for example, refer to Inorg. Chem. Acta, 1994, vol. 222, pp. 85), and the like. Nevertheless, it has been pointed out that such synthetic methods suffer individually from the defects or disadvantages, for example, that rhodium metal used is costly, that even when use is made of ruthenium metal being relatively cheaper than rhodium metal, the ruthenium complex as prepared therefrom is somewhat unstable, while the resultant amine shows a not so much enhanced degree of optical purity, and the like. There were published the research papers reporting that relatively less costly iridium metal is utilized, but in such cases, additives are required to be added in order to produce the highly active catalysts (for example, refer to Angew. Chem. Int. Ed. Engl., 1990, vol. 29, p. 558 and Chem. Lett., 1995, p. 955). Although some research reports were also published on the iridium complexes as prepared without use of additives (for example, refer to J. Am. Chem. Soc., 1990, vol. 112, p. 9400 and Chem. Eur. J., 2004, vol. 10, p. 267), there is confronted the problem that such complexes may merely produce the amines with a lowered degree of optical purity, depending upon the type of substrates used.

It was also reported that when an iridium-carboxylate complex catalyst is used in the asymmetric hydrogenation of imines, optically active amine compounds may be produced in high stereoselectivity and yield, even without use of additives (for example, refer to JP 11-335334-A, Proceedings of the 51$^{st}$ Annual Forum on Complex Chemistry, 327 (2a-A07) (Sept. 28 to 30, 2001), Proceedings I of the 81$^{st}$ Spring Meeting of Chem. Soc. of Japan, 499 (IPB-059) (Mar. 26 to 29, 2002) and Proceedings of Molecular Chirality-2002, 47 (PS-3) (Jun. 6, 2002)). However, there is arisen the problem that even use of such complex results in lowered catalytic activity, although this depends upon the type of substrates used.

DISCLOSURE OF THE INVENTION

[The Problem that the Invention is Intended to Solve]

The object of the present invention is to provide a novel iridium complex. The present invention also has as its object to provide a novel catalyst which may attain improved performance as a catalyst for asymmetric synthesis, especially as a catalyst for asymmetric hydrogenation, in terms of chemical selectivity, enantioselectivity and catalytic activity, etc.

[The Means for Solving the Problem]

The present inventors made intensive investigation into the development of a novel iridium complex and an asymmetric synthesis with use of the same, and as a result, discovered an iridium complex represented by the general formula (1) and also found that asymmetric induction becomes feasible in the reactions using the said complex. These findings were followed by further repeated investigation, leading to completion of the present invention.

Thus, the present invention relates to:

[1] An iridium complex represented by the general formula (1):

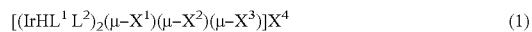

(wherein $L^1$ and $L^2$ may be the same or different and each represent a monodendate neutral ligand, or each cooperate with the other to form a bidendate neutral ligand; $X^1$, $X^2$ and $X^3$ may be the same or different, and each represent a halogen atom; and $X^4$ is a counter-anion),

[2] The iridium complex as described in the above [1], wherein the monodendate neutral ligand or bidendate neutral ligand is optically active,

[3] The iridium complex as described in the above [1], characterized in that the monodendate neutral ligand is a phosphine compound, oxazolines or a nitrogen-containing heterocyclic carbene,

[4] The iridium complex as described in the above [3], characterized in that the phosphine compound is a trialkylphosphine, triarylphosphine or dialkylarylphosphine,

[5] The iridium complex as described in the above [3], characterized in that the oxazolines are a compound represented by the general formula (2):

(wherein $R^1$ and $R^2$ may be the same or different and each represent an alkyl, aryl or heteroaryl group; two of the symbol "*" represent a chiral or non-chiral carbon atom),

[6] The iridium complex as described in the above [3], characterized in that the nitrogen-containing heterocyclic carbene is a compound being selected from the below-described formulae:

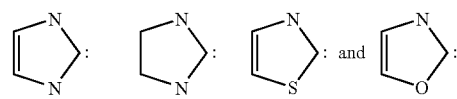

[7] The iridium complex as described in the above [1], characterized in that the bidendate neutral ligand is bisphosphines, diamines, bisoxazolines or biscarbenes,

[8] The iridium complex as described in the above [7], characterized in that the bisphosphines are a compound represented by the general formula (3):

(wherein $R^3$, $R^4$, $R^5$ and $R^6$ each independently represent an alkyl, aryl or heterocyclic group; and $Q^1$ is a divalent group),

[9] The iridium complex as described in the above [7], characterized in that the diamines are a compound represented by the general formula (4):

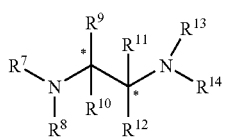

(4)

(wherein $R^7$, $R^8$, $R^{13}$ and $R^{14}$ may be the same or different, and each represent a hydrogen atom or an alkoxycarbonyl or sulfonyl group; $R^9$, $R^{10}$, $R^{11}$ and $R^{12}$ may be the same or different and each represent a hydrogen atom, an alkyl or a monocyclic or polycyclic aromatic hydrocarbon group; $R^9$ and $R^{11}$, or $R^{10}$ and $R^{12}$ each may combine with the other, respectively, to form a ring; and the symbol "*" is a chiral or non-chiral carbon atom),

[10] The iridium complex as described in the above [7], characterized in that the bisoxazolines are a compound represented by the general formula (5):

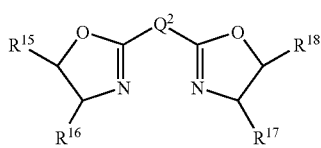

(5)

(wherein $R^{15}$, $R^{16}$, $R^{17}$ and $R^{18}$ each are a hydrogen atom, provided, however, that $R^{15}$ and $R^{16}$ shall not denote a hydrogen atom at the same time and that $R^{17}$ and $R^{18}$ shall not denote a hydrogen atom at the same time), a phenyl group which may be substituted with an alkyl group of 1 to 6 carbon atoms, an alkoxy group of 1 to 6 carbon atoms or a halogen atom, or a benzyl group which may be substituted with an alkyl group(s) of 1 to 6 carbon atoms, an alkoxy group of 1 to 6 carbon atoms or a halogen atom; and $Q^2$ is a phenylene, biphenyldiyl or binaphthalenediyl group, whereby the biphenyldiyl or naphthalenediyl group may have the axial chirality),

[11] The iridium complex as described in the above [7], characterized in that the biscarbenes are a compound represented by the general formula (6):

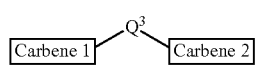

(6)

(wherein $Q^3$ is an alkylene, phenylene, biphenyldiyl or binaphthalenediyl group, whereby the alkylene group may have a chiral carbon atom and the biphenylenediyl or binaphthalenediyl group may possess the axial chirality; and the carbene 1 and carbene 2 may be the same or different, and each represent a nitrogen-containing heterocyclic carbene),

[12] A catalyst, characterized in that the catalyst comprises the iridium complex as described in any one of the above [1] to [11], and

[13] The catalyst as described in the above [12], characterized in that the catalyst is used in the asymmetric hydrogenation.

[Effect of the Invention]

The iridium complex as defined in the present invention, when used as a catalyst, may permit the highly stereoselective reactions to be carried out, thereby producing optically active compounds in high yield. In addition, such optically active compounds are useful as an intermediate for the synthesis of various compounds.

BEST MODE FOR CARRYING OUT THE INVENTION

To be described below is the present invention. It is to be noticed that throughout the present specification, "an alkyl group of 1 to 6 carbon atoms", for example, refers to a methyl, ethyl, n-propyl, isopropyl, n-butyl, sec-butyl, tert-butyl, n-pentyl, 2-pentyl, tert-pentyl, 2-methylbutyl, 3-methylbutyl, 2,2-dimethylpropyl, n-hexyl, 2-hexyl, 3-hexyl, 2-methylpentyl, 3-methylpentyl, 4-methylpentyl, 2-methylpentane-3-yl, cyclopropyl, cyclobutyl, cyclopentyl or cyclohexyl group, etc.; "an alkyl group of 1 to 8 carbon atoms" refers to the above-described alkyl groups of 1 to 6 carbon atoms, and also to a heptyl, octyl or cycloheptyl group, etc.; "an alkyl group of 1 to 10 carbon atoms" refers to the above-described alkyl groups of 1 to 8 carbon atoms, and also to a nonyl or decyl group, etc.; "an alkyl group of 1 to 12 carbon atoms" refers to the above-described alkyl groups of 1 to 10 carbon atoms, and also to a undecyl or dodecyl group, etc.; "an alkyl group of 1 to 15 carbon atoms" refers to the above-described alkyl groups of 1 to 12 carbon atoms, and also to a tridecyl, tetradecyl or pentadecyl group, etc.; and "an alkoxy of 1 to 6 carbon atoms" refers to a methoxy, ethoxy, propoxy, isopropoxy, butoxy, isobutoxy, 2-butoxy, tert-butoxy, pentyloxy, isopentyloxy, 2-methylbutoxy, 3-methylbutoxy, neo-pentyloxy, hexyloxy or cyclohexyloxy group, etc.

The iridium complex of the present invention, as represented by the general formula (1), is a dinuclear iridium-cation type complex having three halogen atoms bridged to two iridium atoms, in which a hydrogen atom and a neutral ligand coordinate individually to the two iridium atoms.

In the general formula (1), the monodendate neutral ligand as represented by $L^1$ and $L^2$ includes, for example, phosphine compounds or heterocyclic compounds, such as oxazolines or nitrogen-containing heterocyclic carbenes.

The phosphine compound is exemplified by monophosphine compounds, such as trialkylphosphines, tri(hetero)arylphosphines or dialkyl(hetero)arylphosphines, etc., and these monophosphine compounds may be either racemates or optically active isomers.

In the above-described phosphine compounds, the alkyl group of the trialkylphosphines includes, for example, straight-chain, branched or cyclic alkyl groups, preferably alkyl groups of 1 to 8 carbon atoms, whereby the respective alkyl groups may be the same or different.

With reference to the above-mentioned phosphine compounds, the tri(hetero)aryl group of the tri(hetero)arylphosphines include, for example, a phenyl, naphthyl, biphenyl, furyl or thieny group, etc., whereby these groups may have a substituent(s), and the respective (hetero)aryl groups may be the same or different, whereby the substituent(s) which allow substitution at the (hetero)aryl group include(s), for example, an alkyl, alkoxy, halogenated alkyl, dialkylamino or alkylenedioxy group, etc. Preferred as the alkyl group are alkyl groups of 1 to 6 carbon atoms, while the alkoxy group includes preferably alkoxy groups of 1 to 6 carbon atoms, and preferable as the halogenated alkyl group are perfluoroalkyl groups and the like, which may be exemplified by a trifluoromethyl or pentafluoroethyl group, etc. The dialkylamino group may be exemplified by dialkylamino groups, such as dimethylamino or diethylamino group, etc., and the alkylenedioxy group includes, for example, a methylenedioxy, ethylenedioxy or isopropylideneoxy group, etc.

Preferred as the oxazolines are racemic or optically active 1,3-oxazolines as represented by the below-illustrated general formula (2):

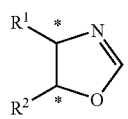
(2)

(wherein $R^1$ and $R^2$ may be the same or different and each represent an alkyl, aryl or heteroaryl group; the two symbols "*" each represent a chiral or non-chiral carbon atom).

The alkyl group represented by $R^1$ and $R^2$ preferably include, for example, straight-chain or branched alkyl groups of 1 to 6 carbon atoms.

Preferred as the aryl group represented by $R^1$ and $R^2$ are aryl groups, such as a phenyl, naphthyl or biphenyl group, and the like, which aryl groups may have a substituent(s). The substituent(s) on the aryl group include(s), for example, alkyl, alkoxy and halogenated alkyl groups or halogen atoms. The alkyl group as the substituent may be exemplified by alkyl groups of 1 to 6 carbon atoms. The alkoxy group as the substituent may be exemplified by alkoxy groups of 1 to 6 carbon atoms. The halogenated alkyl group as the substituent preferably includes, for example, perfluoroalkyl groups and the like, which perfluoroalkyl groups may be exemplified by a trifluoromethyl or pentafluoroethyl group, etc. The halogen atom as the substituent includes, for example, a fluorine or chlorine atom, and the like.

The heteroaryl group represented by $R^1$ and $R^2$ includes, for example, one or two kinds of heteroatoms, such as monocyclic, bicyclic or tricyclic, 5- to 14-membered (preferably 5- to 10-membered) aromatic heterocyclic rings which are substituted for one hydrogen atom and contain, in addition to the carbon atoms, 1 to 4 of one or two kinds of heteroatoms being selected from nitrogen, sulfur and oxygen atoms, and the like. The 5- to 14-membered (preferably 5- to to 10-membered) aromatic heterocyclic rings may be exemplified by aromatic heterocyclic rings, such as thiophene, benzothiophene, benzofuran, benzimidazole, benzoxazole, benzothiazole, benzisothiazole, naphtho[2,3-b]thiophene, furan, phenoxathiin, pyrrole, imidazole, pyrazole, oxathiadiazole, pyridine, pyrazine, pyrimidine, pyridazine, indole, isoindole, 1H-indazole, purine, 4H-quinolizine, isoquinoline, quinoline, phthalazine, naphthylidine, quinoxaline, quinazoline, cinnoline, carbazole, β-carboline, phenanthridine, acridine, phenazine, thiazole, isothiazole, phenothiazine, isooxazole, furazane, phenoxazine, phthalimide, etc., or rings formed by allowing these rings (preferably monocycles) to condense with one or a plural number (preferably 1 or 2) of aromatic rings (e.g., benzene ring, etc.), and the like. The heteroaryl groups are exemplified by thiophene, furan, benzofuran, pyridine or indole, etc. These heteroaryl groups may have the same substituents as the above-mentioned ones on the aryl groups.

The term "nitrogen-containing heterocyclic carbene" refers to carbenes each consisting of a heterocycle containing at least one nitrogen atom, or N-heterocyclic carbenes. The nitrogen-containing heterocyclic carbene preferably includes, for example, carbenes which each have a 5-membered ring structure containing at least one nitrogen atom, as represented by the below-described formulae, whereby the ring structure may have heteroatoms, such as oxygen and sulfur atoms, etc. or a double bond contained or present therein.

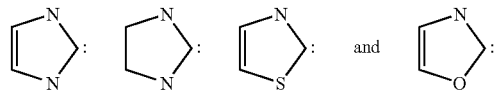

The above-described nitrogen-containing heterocyclic carbenes may have an atom(s) other than the hydrogen atom or a substituent(s) on the non carbenic carbon atom which constitute a ring or on the nitrogen atom which constitutes a ring. The atom other than the hydrogen atom may be exemplified by halogen atoms, such as a fluorine, chlorine, bromine or iodine atom, and the like. The substituent may be exemplified by an alkyl or aryl group, etc., while the substituent may have a chirality.

The alkyl group as a substituent on the above-described nitrogen-containing heterocyclic carbene preferably include, for example, alkyl groups of 1 to 6 carbon atoms, whereby such alkyl groups may be substituted with an alkoxy or phenyl group, etc. When the alkyl group is branched or has a substituent(s), furthermore, the alkyl group may be optically active.

The aryl group as a substituent on the above-described nitrogen-containing heterocyclic carbene may be exemplified by a phenyl group which may have a substituent(s), or a naphthyl group which may have a substituent(s), and the like, whereby the substituent(s) on these aryl groups may be exemplified by an alkyl, alkoxy or dialkylamino group, etc. Referring to the substituents on the aryl groups, the alkyl group preferably is alkyl groups of 1 to 6 carbon atoms, and the alkoxy group preferably is alkoxy groups of 1 to 6 carbon atoms, while the diaminoalkyl group preferably is a dimethylamino or diethylamino group, etc.

The bidentate ligand to be formed by $L^1$ and $L^2$ may be exemplified by bisphosphines, diamines, bisoxazolines or biscarbenes, etc., and such ligands may be either racemic or optically active.

The bisphosphines are represented by the below-described formula (3):

(3)

(wherein $R^3$, $R^4$, $R^5$ and $R^6$ independently each are an alkyl, aryl or heterocyclic group; and $Q^1$ is a divalent group).

The above-mentioned alkyl group represented by $R^3$, $R^4$, $R^5$ and $R^6$ may be either straight-chain, branched or cyclic, and may be exemplified by alkyl groups of 1 to 15 carbon atoms, preferably 1 to 10 carbon atoms, more preferably 1 to 6 carbon atoms.

The above-mentioned aryl group represented by $R^3$, $R^4$, $R^5$ and $R^6$ may be exemplified by aryl groups of 6 to 14 carbon atoms, and their specific examples include a phenyl, naphthyl, anthryl, phenanthryl or biphenyl group, etc. These aryl groups may have a substituent(s), wherein the substituent(s) may be exemplified by alkyl, alkoxy and halogenated alkyl groups or a halogen atom, etc., and the specific examples of such substituents include the ones described for the substituents which are involved in the substitution of the aryl groups represented by $R^1$ and $R^2$.

The above-mentioned heterocyclic group represented by R³, R⁴, R⁵ and R⁶ may be exemplified by aliphatic or aromatic heterocyclic groups. The aliphatic heterocyclic group includes, for example, 5- to 8-membered, preferably 5- or 6-membered monocyclic aliphatic heterocyclic groups and polycyclic or fused rings, which have 2 to 14 carbon atoms and contain as a heteroatom at least one heteroatom, such as a nitrogen, oxygen or sulfur atom. Specific examples of the aliphatic heterocyclic group include a pyrrolidiyl-2-one, piperidino, piperazino, morpholino, tetrahydrofuryl, tetrahydropyranyl or tetrahydrothienyl group. The aromatic heterocyclic group includes, for example, 5- to 8-membered, preferably 5- or 6-membered monocyclic heteroaryl groups and polycyclic or fused ring heteroaryl groups which have 2 to 15 carbon atoms and contain as a heteroatom at least one heteroatom, such as a nitrogen, oxygen or sulfur atom, and their specific examples include a furyl, thienyl, pyridyl, pyrimidyl, pyrazyl, pyridazyl, pyrazolyl, imidazolyl, oxazolyl, thiazolyl, benzofuryl, benzothienyl, quinolyl, isoquinolyl, quinoxalyl, phtharazinyl, quinazolyl, naphthylidyl, cinnolyl, benzoimidazolyl, benzoxazolyl or benzothiazolyl group, and the like.

The divalent group represented by $Q^1$ includes, for example, an alkylene, phenylene, biphenyldiyl or binaphthalenediyl group, and the like. Specifically, the alkylene group preferably includes alkylene groups of 1 to 6 carbon atoms, such as a methylene, ethylene, trimethylene, tetramethylene, pentamethylene or hexamethylene group, and the like. These methylene chains may be substituted with an alkyl, aryl or heterocyclic group represented by R³, R⁴, R⁵ and R⁶. The phenylene group is, for example, an o-, m- or p-phenylene group, whereby the phenylene groups may be substituted with an alkyl, alkoxy, hydroxyl, amino or substituted amino group, etc. The biphenyldiyl or naphthalenediyl group preferably includes, for example, the ones having a 1,1'-biaryl-2,2'-diyl type structure, and the biphenyldiyl or binaphthalenediyl group may be substituted with an alkyl group(s) of 1 to 6 carbon atoms, an alkoxy group(s) of 1 to 6 carbon toms, a hydroxyl group(s), an amino group(s) or a substituted amino group(s), and may be partially hydrogenated.

As the bisphosphines represented by the general formula (3), the optically active bisphosphines are more preferable, among the above-described phosphines. To be furthermore described below are the optically active bisphosphines.

The optically active bisphosphines include, for example, the bisphosphines which have been known prior to filing of the present patent application, one of which may be exemplified by the phosphines represented by the general formula (7):

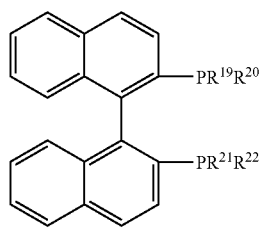

(7)

(wherein $R^{19}$, $R^{20}$, $R^{21}$ and $R^{22}$ may the same or different, and each represent a cycloalkyl group, or a phenyl group which may be substituted with an alkyl group of 1 to 6 carbon atoms, an alkoxy group of 1 to 6 carbon atoms or a halogen atom (e.g., fluorine or chlorine, etc.). The cycloalkyl group represented by $R^{19}$, $R^{20}$, $R^{21}$ and $R^{22}$ preferably includes a cyclopentyl or cyclohexyl group.

As specific examples of the optically active bisphosphines represented by the general formula (7), there may be mentioned 2,2'-bis-(diphenylphosphino)-1,1'-binaphthyl (hereinafter referred to briefly as "BINAP"), 2,2'-bis-(di-p-tolylphosphino)-1,1'-binaphthyl (hereinafter referred to briefly as "Tol-BINAP"), 2,2'-bis-(di-m-tolylphosphino)-1,1'-binaphthyl, 2,2'-bis-(di-(3,5-xylyl)phosphino)-1,1'-binaphthyl (hereinafter referred to briefly as "DM-BINAP"), 2,2'-bis-(di-t-butylphenylphosphino)-1,1'-binaphthyl, 2,2'-bis-(di-p-methoxyphenylphosphino)-1,1'-binaphthyl, 2,2'-bis-(di-p-chlorophenylphosphino)-1,1'-binaphthyl, 2,2'-bis-(dicyclopentylphosphino)-1,1'-binaphthyl ("Cp-BINAP") or 2,2'-bis-(dicyclohexylphosphino)-1,1'-binaphthyl ("Cy-BINAP"), and the like.

As one of the optically active bisphosphines, additionally, there may be mentioned bisphosphines represented by the general formula (8):

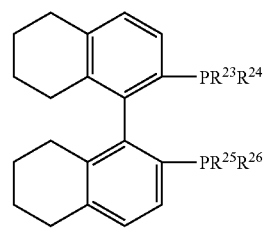

(8)

(wherein $R^{23}$, $R^{24}$, $R^{25}$ and $R^{26}$ may be the same or different, and each represent a cycloalkyl group, or a phenyl group which may be substituted with an alkyl groups(s) of 1 to 6 carbon atoms, an alkoxy group(s) of 1 to 6 carbon atoms or a halogen atom(s)). The cycloalkyl group represented by $R^{23}$, $R^{24}$, $R^{25}$ and $R^{26}$ preferably is a cyclopentyl or cyclohexyl group.

Specific examples of the optically active bisphosphines represented by the general formula (8) include 2,2'-bis(diphenylphosphino)-5,5',6,6',7,7',8,8'-octahydro-1,1'-binaphthyl (hereinafter referred to briefly as "H₈-BINAP"), 2,2'-bis(di-p-tolylphosphino)-5,5',6,6',7,7',8,8'-octahydro-1,1'-binaphthyl, 2,2'-bis(di-m-tolylphosphino)-5,5',6,6',7,7',8,8'-octahydro-1,1'-binaphthyl, 2,2'-bis(di(3,5-xylyl)phosphino)-5,5',6,6',7,7',8,8'-octahydro-1,1'-binaphthyl, 2,2'-bis(di-t-butylphosphino)-5,5',6,6',7,7',8,8'-octahydro-1,1'-binaphthyl, 2,2'-bis(di-p-methoxyphenylphosphino)-5,5',6,6',7,7',8,8'-octahydro-1,1'-binaphthyl, 2,2'-bis(di-p-chlorophenylphosphino)-5,5',6,6',7,7',8,8'-octahydro-1,1'-binaphthyl, 2,2'-bis(dicyclopentyl-phosphino)-5,5',6,6',7,7',8,8'-octahydro-1,1'-binaphthyl, Or 2,2'-bis(dicyclohexylphosphino)-5,5',6,6',7,7',8,8'-octahydro-1,1'-binaphthyl, etc.

As one of the optically active bisphosphines, furthermore, there may be mentioned bisphosphines represented by the general formula (9):

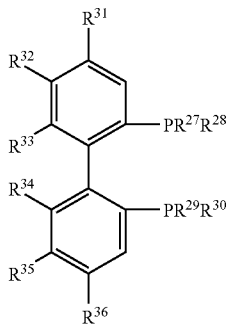

(9)

(wherein $R^{27}$, $R^{28}$, $R^{29}$ and $R^{30}$ may be the same or different, and each represent a cycloalkyl group, or a phenyl group which may be substituted with an alkyl group(s) of 1 to 6 carbon atoms, an alkoxy group(s) of 1 to 6 carbon atoms or a halogen atom(s); and $R^{31}$, $R^{32}$, $R^{33}$, $R^{34}$, $R^{35}$ and $R^{36}$ may be the same or different, and each represent a hydrogen atom, an alkyl group of 1 to 6 carbon atoms or an alkoxy group of 1 to 6 carbon atoms, and any two groups out of $R^{31}$, $R^{32}$ and $R^{33}$ may bond to each other to form a 5- to 6-membered ring which may have oxygen at a constituent atom, or any two groups out of $R^{34}$, $R^{35}$ and $R^{36}$ may bond to each other to form a similar ring, provided, however, that $R^{33}$ and $R^{34}$ shall not constitute a hydrogen atom). Preferable as the cycloalkyl group represented by $R^{27}$, $R^{28}$, $R^{29}$ and $R^{30}$ are a cyclopentyl or cyclohexyl group.

Specific examples of the optically active bisphosphines represented by the general formula (9) include ((4,4'-bi-1,3-benzodioxole)-5,5'-diyl)bis(diphenylphosphine) (SEGPHOS), (4,4'-bi-1,3-benzodioxole)-5,5'-diyl)bis(di(3,5-xylyl)phosphine) (DM-SEGPHOS), ((4,4'-bi-1,3-benzodioxole)-5,5'-diyl)bis(bis(3,5-di-t-butyl-4-methoxyphenyl)phosphine) (DTBM-SEGPHOS), ((4,4'-bi-1,3-benzodioxole)-5,5'-diyl)bis(bis(4-methoxyphenyl) phosphine), ((4,4'-bi-1,3-benzodioxol)-5,5'-diyl)bis (dicyclohexylphosphine) (Cy-SEGPHOS), ((4,4'-bi-1,3-benzodioxole)-5,5'-diyl)bis(bis(3,5-di-t-butylphenyl) phosphine), 2,2'-bis(diphenylphosphino)-4,4',6,6'-tetramethyl-5,5'-dimethoxy-1,1'-biphenyl, 2,2'-bis(di-p-methoxyphenyl-phosphino)-4,4',6,6'-tetramethyl-5,5'-dimethoxy-1,1'-biphenyl, 2,2'-bis(diphenylphosphino)-4,4', 6,6'-tetra(trifluoromethyl)-5,5'-dimethyl-1,1'-biphenyl, 2,2'-bis(diphenylphosphino)-4,6-di(trifluoromethyl)-4',6'-dimethyl-5'-methoxy-1,1'-biphenyl, 2-dicyclohexyl-phosphino-2'-diphenylphosphino-4,4',6,6'-tetramethyl-5,5'-dimethoxy-1,1'-biphenyl, 2,2'-bis(diphenylphosphino)-6,6'-dimethyl-1,1'-biphenyl, 2,2'-bis(diphenylphosphino)-4,4',6, 6'-tetramethyl-1,1'-biphenyl, 2,2'-bis(diphenylphosphino)-3, 3',6,6'-tetramethyl-1,1'-biphenyl, 2,2'-bis (diphenylphosphino)-4,4'-difluoro-6,6'-dimethyl-1,1'-biphenyl, 2,2'-bis(diphenylphosphino)-4,4'-bis (dimethylamino)-6,6'-dimethyl-1,1'-biphenyl, 2,2'-bis(di-p-tolylphosphino)-6,6'-dimethyl-1,1'-biphenyl, 2,2'-bis(di-o-tolylphosphino)-6,6'-dimethyl-1,1'-biphenyl, 2,2'-bis(di-m-fluorophenylphosphino)-6,6'-dimethyl-1,1'-biphenyl, 1,11-bis(diphenylphosphino)-5,7-dihydrobenzo[c,e]oxepine, 2,2'-bis(diphenylphosphino)-6,6'-dimethoxy-1,1'-biphenyl, 2,2'-bis(diphenylphosphino)-5,5',6,6'-tetramethoxy-1,1'-biphenyl, 2,2'-bis(di-tolylphosphino)-6,6'-dimethoxyl-1,1'-biphenyl or 2,2'-bis(diphenylphosphino)-4,4',5,5',6,6'-hexamethoxy-1,1'-biphenyl, etc.

The miscellaneous optically active bisphosphines which may be furthermore used in the present invention include, for example, N,N-dimethyl-1[1',2-bis(diphenylphosphino)ferrocenyl]ethylamine, 2,3-bis(diphenylphosphino)butane, 1-cyclohexyl-1,2-bis(diphenylhosphino)ethane, 2,3-O-isopropyliden-2,3-dihydroxy-1,4-bis(diphenylphosphino)butane, 1,2-bis{(o-methoxyphenyl)phenylphosphino)ethane, 1,2-bis(2,5-dialkylphospholano)benzene, 1,2-bis(2,5-dialkylphospholano)ethane, 1-(2,5-dialkylphospholano)-2-(diphenylphosphino)benzene, 1-(2,5-dialkylphospholano)-2-(di(alkylphenyl)phosphino)benzene, 5,6-bis(diphenylphosphino)-2-norbornene, N,N'-bis(diphenylphosphino)-N,N'-bis(1-phenylethyl) ethylenediamine, 1,2-bis(diphenylphosphino)propane or 2,4-bis(diphenylphosphino)pentane and the like. Naturally, the optically active bisphosphines which may be used in the present invention are not understood to be limited to them, and the particularly preferable, optically active bisphosphines are the optically active bisphosphines represented by the general formula (7), with BINAP, Tol-BINAP, DM-BINAP, $H_8$-BINAP, SEGPHOS, DM-SEGPHOS or DTBM-SEGPHOS, etc. being especially preferred.

The amines in the bidentate ligands include, for example, the diamines represented by the general formula (4):

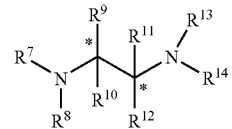

(4)

(wherein $R^7$, $R^8$, $R^{13}$ and $R^{14}$ each are a hydrogen atom, or a alkoxycarbonyl or sulfonyl group; $R^9$, $R^{10}$, $R^{11}$ and $R^{12}$ may be the same or different, and each represent a hydrogen atom, an alkyl group or a monocylic or polycyclic aromatic hydrocarbon group; the two group of $R^9$ and $R^{11}$, and $R^{10}$ and $R^{12}$ may bond to each other to form a ring, respectively; the mark "*" represents a chiral carbon atom or non-chiral carbon atom).

The saturated hydrocarbon group represented by $R^7$, $R^8$, $R^{13}$ and $R^{14}$ includes, for example, straight-chain, branched or cyclic alkyl groups of 1 to 6 carbon atoms, while the unsaturated hydrocarbon group is exemplified by alkenyl groups or alkynyl groups of 2 to 6 carbon atoms, such as a vinyl, propargyl, propenyl or butynyl group, with the aryl group being exemplified by aryl groups of 6 to 12 carbon atoms, such as a phenyl or naphthyl group.

The alkyl group represented by $R^9$, $R^{10}$, $R^{11}$ and $R^{12}$ preferably includes straight-chain, branched or cyclic alkyl groups of 1 to 8 carbon atoms, and the monocyclic or polycyclic aromatic hydrocarbon group is preferably exemplified by aryl groups, such as a phenyl, tolyl (o-, m-, p-), xylyl or naphthyl group, etc., while the unsaturated hydrocarbon group preferably includes, for example, alkenyl or alkynyl groups of 2 to 6 carbon atoms, such as a vinyl, propargyl, propenyl or butynyl group, etc. The ring formed by either $R^9$ and $R^{11}$, or $R^{10}$ and $R^{12}$ includes, for example, rings of 3 to 8 carbon atoms, such as cyclopropane, cyclobutane, cyclopentane, cyclohexane, cycloheptane, cyclooctane, etc.

Specific examples of the diamine include 1,2-diphenylethylenediamine, 1,2-cyclohexanediamine, 1,2-cycloheptanediamine, 2,3-dimethylheptanediamine, 1-methyl-2,2-diphenylethylenediamine, 1-isobutyl-2,2-diphenylethylenediamine, 1-isopropyl-2,2- diphenylethylene-diamine, 1-methyl-2,2-di(p-methoxyphenyl)ethylenediamine, 1-isobutyl-2,2-di(p-methoxyphenyl)ethylenediamine, 1-isopropyl-di(p-methoxyphenyl)ethylenediamine, 1-benzyl-2,2-di(p-methoxyphenyl)ethylenediamine, 1-methyl-2,2-dinaphthylethylenediamine, 1-isobutyl-2,2-dinaphthylethylenediamine or 1-isopropyl-2,2-dinaphthylethylenediamine, N-methoxycarbonyl-1,2-diphenylethylenediamine, N-(p-toluenesulfonyl)-1,2-diphenylethylenediamine or N-methanesulfonyl-1,2-diphenylethylenediamine, etc., and these diamines may be either racemic or optically active.

The bisoxazolines in the bidentate ligands are exemplified by the bisoxazolines represented by the below-illustrated formula (5):

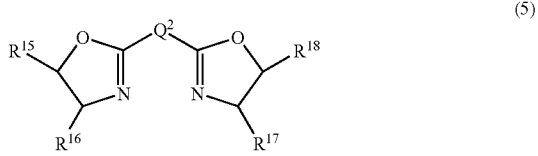

(5)

(wherein $R^{15}$, $R^{16}$, $R^{17}$ and $R^{18}$ each are a hydrogen atom (provided, however, that $R^{15}$ and $R^{16}$ each shall not denote a hydrogen atom at the same time, while $R^{17}$ and $R^{18}$ each shall not denote a hydrogen atom at the same time), a phenyl group which may be substituted with an alkyl group(s) of 1 to 6 carbon atoms, an alkoxy group(s) of 1 to 6 carbon atoms or a halogen atom(s), or a benzyl group which may be substituted with an alkyl group(s) of 1 to 6 carbon atoms, an alkoxy group(s) of 1 to 6 carbon atoms or a halogen atom(s); and $Q^2$ is a phenylene, biphenyldiyl or binaphthalenediyl group, whereby the biphenyldiyl or binaphthalenediyl group may have the axial chirality). These bisoxazolines may be either racemic or optically active.

The carbene in the bidentate ligands includes, for example, the biscarbenes represented by the below-illustrated general formula (6):

(6)

(wherein $Q^3$ represents an alkylene, phenylene, biphenyldiyl or binaphthalenediyl group, whereby the alkylene group may have a chiral carbon atom, and the biphenyldiyl or binaphthalenediyl group may have the axial chirality; "Carbene 1" and "Carbene 2" may be the same or different, and each represent a nitrogen-containing heterocyclic carbene).

The alkylene group represented by $Q^3$ is preferably exemplified by the same alkyl groups as the ones represented by $Q^1$.

The nitrogen-containing heterocyclic carbene represented by "Carbene 1" and "Carbene 2" denotes carbenes each consisting of a heterocyclic ring containing at least one nitrogen atom or N-heterocyclic carbenes, and the like. The heterocyclic carbenes preferably include the ones each having a 5-membered ring structure containing at least one nitrogen atom as represented by the below-illustrated formulae:

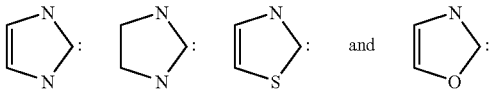

The ring structures may have such heteroatoms as oxygen or sulfur atom, etc., and a double bond being present therein.

The nitrogen-containing heterocyclic carbenes, which are linked to $Q^3$ on the ring-constituting non carbenic carbon atom and on the ring-constituting nitrogen atom, may have atoms other than hydrogen atom or substituents at the positions which are not linked to $Q^3$. Atoms other than hydrogen atom include, for example, halogen atoms, such as a fluorine, chlorine, bromine or iodine atom, etc., while the substituents are exemplified by alkyl or aryl groups, etc. Additionally, such substituents may have the chirality.

The alkyl group as a substituent on the nitrogen-containing heterocyclic carbene preferably include alkyl groups of 1 to 6 carbon atoms, which may be substituted with alkoxy groups of 1 to 6 carbon atoms or a phenyl group, etc. when the alkyl group is branched or has substituents, the alkyl group may be optically active.

The aryl group as a substituent on the nitrogen-containing heterocyclic carbenes preferably include phenyl groups which may have substituents or naphthyl groups which may have substituents, and the like. The substituents on the aryl group may be exemplified by alkyl, alkoxy or dialkylamino groups, etc. In the substituents on the aryl group, the alkyl groups are preferably alkyl groups of 1 to 6 carbon atoms, while the alkoxy groups are preferably alkoxy groups of 1 to 6 carbon atoms, and the dialkylamino groups are preferably dimethylamino or diethylamino group, etc.

These biscarbenes may be either racemic or optically active. The above-mentioned neutral ligands are partly available as a commercialized reagent in the forms of the ligands themselves or precursors for the ligands, and may also be produced in accordance with the methods described in the relevant prior literature references, etc.

The halogen atoms represented by $X^1$, $X^2$ and $X^3$ include, for example, fluorine, chlorine, bromine or iodine, etc.

The counter-anions represented by $X^4$ comprehend monovalent anionic ligands and may be exemplified by $F^-$, $Br^-$, $Cl^-$, $I^-$, $I_3^-$, $CF_3SO_3^-$, $p\text{-}CH_3C_6H_4SO_3^-$, $ClO_4^-$, $NO_3^-$, $BF_4^-$, $B(C_6H_5)_4^-$, $B[3,5\text{-}(CF_3)_2C_6H_3]_3^-$, $PF_6^-$, $SbF_6^-$ or $AsF_6^-$, etc.

The iridium complex of the present invention may be produced by reacting an iridium compound with the above-mentioned monodentate neutral ligand or bidentate neutral ligand, followed by reaction with a hydrogen halide or hydrohalo acid.

The above-described iridium compound includes, for example, di-μ-chlorotetrakis(cyclooctene)diiridium ([IrCl(coe)$_2$]$_2$), di-μ-bromotetrakis(cyclooctene)diiridium ([IrBr(coe)$_2$]$_2$), di-μ-iodotetrakis(cyclooctene)diiridium ([IrI(coe)$_2$]$_2$), di-μ-chlorobis(1,5-cyclooctadiene)diiridium ([IrCl(cod)]$_2$), di-μ-bromobis(1,5-cyclooctadiene)diiridium ([IrBr(cod)]$_2$), di-μ-iodobis(1,5-cyclooctadiene)diiridium ([IrI(cod)]$_2$), di-p-chlorobis(bicyclo[2,2,1]hepta-2,5-diene)diiridium ([IrCl(nbd)]$_2$), di-p-bromobis(bicyclo[2,2,1]hepta-2,5-diene)diiridium ([IrBr(nbd)]$_2$) or di-p-iodobis(bicyclo[2,2,1]hepta-2,5-diene)diiridium ([IrI(nbd)]$_2$), etc.

The iridium complex of the present invention may be produced by reacting one of these iridium compounds with the above-mentioned monodentate neutral ligand or bidentate neutral ligand, followed by reaction with a hydrogen halide or hydrohalo acid.

The above-mentioned hydrogen halide includes, for example, hydrogen fluoride, hydrogen chloride, hydrogen bromide, hydrogen iodide, etc., and the hydrohalo acid may be exemplified by hydrofluoric acid, hydrochloric acid, hydrobromic acid, hydroiodic acid, etc. The amount of the monodentate or bidentate neutral ligand to be used for iridium atom of the iridium compound may be selected from about 2-fold molar amount of the monodentate neutral ligand or about equimolar amount of the bidentate neutral ligand.

Furthermore, the iridium complex of the present invention may be produced by reacting an iridium complex represented by the below-illustrated general formula (10):

(wherein $Y^1$ is a halogen atom; $Y^2$ is an organic acid residue; and other groups are as defined above) or by the below-illustrated general formula (11):

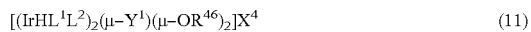

(wherein $R^{46}$ is a hydrogen atom, an alkyl group which may have substituents, a (hetero)aryl group which may have substituents, or an aralkyl group which may have substituents; other groups are as defined above) with a hydrogen halide or hydrohalo acid.

The compounds represented by the general formula (10) may be synthesized, for example, in accordance with the methods described in JP 11-335334-A, the Proceedings of the 51st Annual Meeting on the Discussions of the Chemistry of Complexes, p. 327 (2a-A07) (held during Sep. 28 to Sep. 30, 2001), the Proceedings I of the 81st Spring Annual Meeting of the Chemical Society of Japan, p. 499 (1PB-059) (held during Mar. 26 to Mar. 29, 2002) and the Proceedings of Molecular Chirality 2002, p. 47 (PS-3) (held on Jun. 6, 2002).

The organic acid residue represented by $Y^2$ in the above-illustrated general formula (10) refers to the compounds of a chemical structure having one hydrogen atom eliminated as a proton from an organic acid, and their specific examples include carboxylic acid residues ($R^{47}CO_2$), sulfonic acid residues ($R^{48}SO_3$) and phosphoric acid residues (($R^{49})_2PO_2$).

The symbol $R^{47}$ in the carboxylic acid residues $R^{47}CO_2$ may be exemplified by a hydrogen atom, an optionally substituted alkyl group of 1 to 3 carbon atoms, an optionally substituted phenyl or naphthyl group, etc., whereby a substitute on the optionally substituted alkyl group of 1 to 3 carbon atoms includes, for example, alkyl groups of 1 to 4 carbon atoms and halogen atoms. Specific examples of the optionally substituted alkyl group of 1 to 3 carbon atoms include methyl, ethyl, propyl, pivalyl and trifluoromethyl groups. The substituent on the optionally substituted phenyl or naphthyl group may be exemplified by methyl, ethyl, n-propyl, methoxy, ethoxy and propoxy groups, and halogen atoms.

The symbol $R^{48}$ in the sulfonic acid residues $R^{48}SO_3$ may be exemplified by alkyl groups of 1 to 12 carbon atoms, and optionally substituted phenyl or naphthyl groups.

The symbol $R^{49}$ in the phosphoric acid residues (($R^{49})_2PO_2$) may be exemplified by optionally substituted alkoxy groups of 1 to 6 carbon atoms, optionally substituted phenoxy groups, and optionally substituted phenyl or naphthyl groups, and furthermore includes the groups which two $R^{49}$s may combine to form. The optionally substituted phenyl or naphthyl groups include, for example, (biphenyl-2,2'-diyl)dioxy group, (1,1'-binaphthyl-2,2'-diyl)dioxy group, etc., and substituents on the optionally substituted phenyl or naphthyl groups may be exemplified by methyl, ethyl, propyl, methoxy, ethoxy and propoxy groups, halogen atoms, etc.

The compounds represented by the general formula (11) may be synthesized, for example, in accordance with the method described in Angew. Chem. Int. Ed., 1998, vol. 37, p. 3381-3383.

The alkyl group as $R^{46}$ in the compounds represented by the above general formula (11) includes, for example, alkyl groups of 1 to 8 carbon atoms, and the (hetero)aryl group may be exemplified by phenyl, naphthyl, pyridyl, pyrimidyl, furyl, thienyl, etc., whereby the substituent on these groups includes, for example, alkyl groups of 1 to 6 carbon atoms, alkoxy groups of 1 to 6 carbon atoms, halogen atoms, such as fluorine, chlorine and bromine atoms, etc.; the alkyl moiety in the aralkyl group as $R^{46}$ may be exemplified by alkyl groups of 1 to 12 carbon atoms, whereby the substituent includes, for example, alkoxy groups of 1 to 6, halogen atoms, such as a fluorine, chlorine or bromine atom, etc.

These reactions are preferably carried out in a solvent. Specific examples of the solvent include aromatic hydrocarbon solvents, such as toluene or xylene, etc., aliphatic hydrocarbon solvents, such as hexane or heptane, etc., halogen-containing hydrocarbon solvents, such as methylene chloride, etc., alcohol solvents, such as methanol, ethanol or 2-propanol, etc., ether solvents, such as diethyl ether, tetrahydrofuran or 1,4-dioxane, etc., organic solvents, such as acetonitrile, dimethylformamide or dimethyl sulfoxide, etc., and the like. These solvents are preferably used singly or as a solvent mixture of not less than two thereof.

The above-mentioned hydrogen halide or hydrohalo acid may be exemplified by hydrogen halides, such as hydrogen chloride, hydrogen bromide, hydrogen iodide, etc., and hydrohalo acids, such as hydrochloric acid, hydrobromic acid or hydroiodic acid, etc., and hydrohalo acids are preferred in view of their enhanced ease of handling. The amount of these hydrogen halides or hydrohalo acids as used is preferably in the range of up to about 10 equivalent amounts of iridium atom.

The counter-anions of the iridium complexes as obtained in the above-described manner may be subjected to replacement of their halogen atoms with miscellaneous atomic groups. The replaceable atomic groups may be exemplified by $BF_4^-$, $ClO_4^-$, $CF_3SO_3^-$, (hereinafter referred to as "OTf"), $PF_6^-$, $SbF_6^-$, $BPh_4^-$, $p\text{-}CH_3C_6H_4SO^{3-}$, $NO_3^-$, $B[3,5\text{-}(CF_3)_2C_6H_3]_3^-$, or $AsF_6^-$, etc.

The iridium complexes of the present invention as obtained in this manner, especially the iridium complexes having the optically active ligands, can suitably be used for the production of optically active compounds. The specific reactions to be applied to the production of optically active compounds include, for example, asymmetric 1,4-addition reaction, asymmetric hydroformylation, asymmetric hydrocyanation, asymmetric hydroamination, asymmetric Heck reaction, or asymmetric hydrogenation, etc. In particular, the asymmetric hydrogenation is advantageously utilized.

Examples of the asymmetric hydrogenation include asymmetric hydrogenation for prochiral carbon-carbon double bonds, such as prochiral enamines, olefins or enol-ethers, etc., prochiral carbon-oxygen double bonds, such as prochiral ketones, etc., and prochiral carbon-nitrogen double bonds, such as prochiral imines, etc.

To be described below is the asymmetric hydrogenation.

The asymmetric hydrogenation for compounds having the above-mentioned carbon-carbon double bonds may be exemplified by the reaction for olefin compounds represented by the reaction scheme (12):

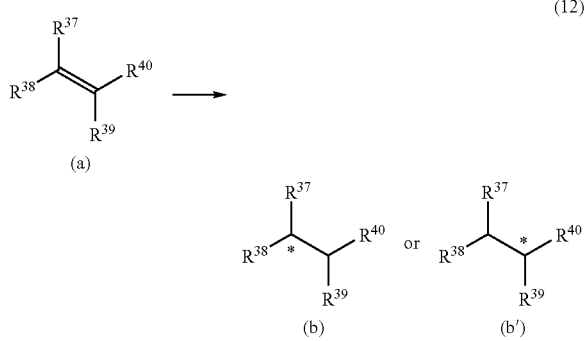

(wherein $R^{37}$, $R^{38}$, $R^{39}$ and $R^{40}$ each are an optionally substituted alkyl group, an optionally substituted (hetero)aryl, optionally substituted aralkyl, acyl, carboxyl, alkoxycarbonyl, optionally substituted carbamoyl, cyano, acylamino or amino group, and additionally, $R^{37}$ and $R^{38}$ or $R^{39}$ and $R^{40}$ each are different from the other; $R^{37}$ and $R^{39}$, $R^{37}$ and $R^{40}$ or $R^{39}$ and $R^{40}$ individually are taken together to form a dissymmetric cyclic structure as the whole; and the symbol "*" denotes a chiral carbon atom).

The alkyl group in $R^{37}$, $R^{38}$, $R^{39}$ and $R^{40}$ as mentioned above includes alkyl groups of 1 to 8 carbon atoms. The (hetero)aryl group may be exemplified by a phenyl, naphthyl, pyridyl, pyrimidyl, furyl or thienyl group, etc., while the substituent includes, for example, alkyl groups of 1 to 6 carbon atoms, alkoxy groups of 1 to 6 carbon atoms and halogen atoms, such as a fluorine, chlorine or bromine atom, etc., and the like. In the substituents for the aralkyl group, the alkyl group may be exemplified by alkyl groups of 1 to 12 carbon atoms. The acyl group includes, for example, an acetyl, propanoyl, butyryl, pivaloyl or benzoyl group, etc. The alkoxycarbonyl group may be exemplified by a methoxycarbonyl, ethoxycarbonyl, n-propoxycarbonyl, isopropoxycarbonyl, tert-butoxycarbonyl or benzyloxycarbonyl group, etc. The substituted carbamoyl group includes, for example, a dimethylcarbamoyl, diethylcarbamoyl or dibenzylcarbamoyl group, etc. The acylamino group may be exemplified by an acetylamino, tert-butoxycarbonylamino or benzyloxycarbonylamino group, etc. And in the case of the dissymmetric cyclic structure being formed as the whole, such structure may preferably be 5-membered or 6-membered cyclic structures.

In the organic compounds having a multiple bond, the asymmetric hydrogenation reaction for a compound having a carbon-oxygen double bond may be exemplified by the reaction for a ketone compound represented by the scheme (13):

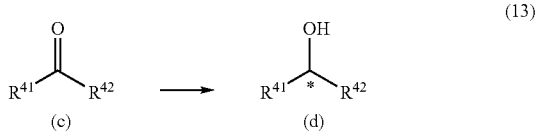

(wherein $R^{41}$ and $R^{42}$ each are different from the other, and each represent an optionally substituted alkyl, optionally substituted (hetero)aryl or optionally substituted aralkyl group; $R^{41}$ and $R^{42}$ may be taken together to form a dissymmetric cyclic ketone as the whole; the symbol "*" denotes a chiral carbon atom), while the asymmetric hydrogenation for a compound having a carbon-nitrogen double bond may be exemplified by the reaction for an imine compound represented by the scheme (14):

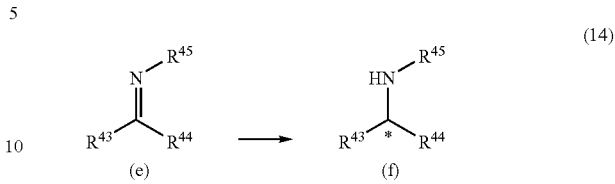

(wherein $R^{43}$ and $R^{44}$ each are different from the other, and each represent an optionally substituted alkyl, optionally substituted (hetero)aryl or optionally substituted aralkyl group; $R^{43}$ and $R^{44}$, $R^{43}$ and $R^{45}$ or $R^{44}$ and $R^{45}$ may form a dissymmetric cyclic imine; the symbol "*" denotes a chiral carbon atom).

The alkyl group as the above-described $R^{41}$ and $R^{42}$ or $R^{43}$, $R^{44}$ and $R^{45}$ in the compound represented by the general formula (14) includes, for example, alkyl groups of 1 to 8 carbon atoms, and the (hetero)aryl group may be exemplified by a phenyl, naphthyl, pyridyl, pyrimidinyl, furyl or thienyl group, etc., whereby as the substituent, for example, there may be mentioned alkyl groups of 1 to 6 carbon atoms, alkoxy groups of 1 to 6 carbon atoms or halogen atoms, and the like. Referring to the substituent for the aralkyl group, the alkyl group includes alkyl groups of 1 to 12 carbon atoms. In cases where $R^{41}$ and $R^{42}$ are taken together to form a cyclic structure, the optionally substituted cyclic ketone as represented by the general formula (13) may be exemplified by compounds having a cycloalkanone structure or cycloalkenone structure of 3 to 8 carbon atoms, 1-indanone structure, 2-indanone structure, 1-tetralone structure, 2-tetralone structure or 1-benzosuberone structure, etc., whereby the substituent may be exemplified by alkyl groups of 1 to 6 carbon atoms, alkoxy groups of 1 to 6 carbon atoms, halogen atoms or aryl groups, etc.

The compound in which two groups each of $R^{43}$ and $R^{44}$, $R^{43}$ and $R^{45}$ or $R^{44}$ and $R^{45}$ cooperate to form a dissymmetric cyclic imine includes, for example, compounds having a 3,4-dihydro-2H-pyrrole structure, 2,3,4,5-tetrahydropyridine structure, 3H-indole structure, 3,4-dihydroquinoline structure or 3,4-dihydroisoquinoline structure, etc., whereby the substituent may be exemplified by alkyl groups of 1 to 6 carbon atoms, alkoxy groups of 1 to 6 carbon atoms, halogen atoms or aryl groups, etc.

Specific examples of the compounds represented by (c) in the above-illustrated scheme (13) include acetophenone, propiophenone, butyrophenone, isobutyrophenone, chloromethylphenyl ketone, bromomethylphenyl ketone, 2-acetylpyridine, 3-acetylpyridine, (o-methoxy)acetophenone, (o-ethoxy)acetophenone, (o-propoxy)acetophenone, (o-benzyloxy)acetophenone, α-acetonaphthone, p-chlorophenyl methyl ketone, p-bromophenyl methyl ketone, p-cyanophenyl methyl ketone, phenyl benzyl ketone, phenyl(o-tolylmethyl)ketone, phenyl(m-tolylmethyl)ketone, phenyl(p-tolylmethyl)ketone, 2-butanone, 2-pentanone, 2-hexanone, 2-heptanone, 2-octanone, 2-nonanone, 2-decanone, cyclohexyl methyl ketone, cyclohexyl ethyl ketone, cyclohexyl benzyl ketone, t-butyl methyl ketone, 3-quinuclidinone, 1-indanone, 2-indanone, 1-tetralone, 2-tetralone, benzyl(2-pyridyl)ketone, benzyl(3-pyridyl)ketone or benzyl(2-thiazolyl) ketone, and the like.

Specific examples of the compounds represented by (e) in the above-illustrated scheme (14) include 3,4-dihydro-5-phenyl-2H-pyrrole, 6-phenyl-2,3,4,5-tetrahydropyridine, 1-methyl-3,4-dihydroisoquinoline, 6,7-dimethoxy-1-methyl-3,4-dihydroisoquinoline, 1-phenyl-3,4-dihydroisoquinoline, 1-methyl-3,4-dihydro-9H-pyrido[3,4-b]indole or α-methylbenzylidenebenzylamine, etc.

The iridium complexes of the present invention are useful for reduction of the multiple bonds of organic compounds, particularly as a reduction catalyst for carbon-carbon double bonds or carbon-heteroatom double bonds. Furthermore, the iridium complexes of the present invention, by rendering their ligands optically active, can find useful application as a catalyst for the asymmetric hydrogenation. The iridium complexes of the present invention, when utilized as a catalyst, may be used after increasing their purity, for example, by the purification procedures, such as concentration, concentration in vacuo, solvent extraction, washing, recrystallization, etc., following the synthesis of said iridium complexes, and may also be utilized as a reduction catalyst without purification.

In the preferred embodiment of the present invention, the asymmetric hydrogenation is carried out by dissolving a substrate to be hydrogenated in a solvent which does not inhibit the asymmetric hydrogenation, such as alcohol solvents, e.g. methanol, ethanol or 2-propanol, etc., tetrahydrofuran, diethyl ether, methylene chloride, acetone, ethyl acetate, benzene, toluene, N,N-dimethylformamide, acetonitrile or a solvent mixture thereof, and the like, followed by addition of the catalyst of the present invention at ratios of about 1/10 to 1/10,000 moles, preferably about 1/50 to 1/3,000 moles, for the substrate, and maintaining the reaction solution at temperatures of about −20 to 100° C., preferably about 20 to 80° C., under hydrogen pressure kept at about 1 to 10 MPa, preferably about 3 to 7 MPa, for a length of time of about 0.5 to 30 hours, preferably about 1 to 20 hours.

To be given below are the examples to illustrate the present invention, but the present invention is not understood to be limited thereto, whereby use was made of the below-described units of analytical equipment.

For nuclear magnetic resonance (NMR): MERCURY 300-C/H (VARIAN)

For melting point (mp): MP-500 (Yanako) For infrared absorption spectrum (IR): FT/IR-230 (JASCO Corp.)

For Gas chromatography (GLC): GC-14A (Shimadzu Corp.)

EXAMPLE 1

Synthesis of [{IrH((S)-BINAP)}$_2$(μ-I)$_3$]I

A 33.5 mg (0.0392 mmol) quantity of [IrI(cod)]$_2$ and 5 mL of toluene were placed in a 20-mL Schlenk tube under an argon atmosphere, followed by stirring. To the resultant solution was added 53.7 mg (0.0862 mmol) of (S)-BINAP, followed by stirring at room temperature for 3 hours, and 28.5 μL (0.196 mmol, 5.0 equivalents) of 55% hydroiodic acid was added to the reaction mixture, followed by stirring at room temperature overnight. The solvent was removed under reduced pressure, and the resultant residue was recrystallized from dichloromethane-hexane to give the subject title compound (66.0 mg, pale yellow solid). It meanwhile is to be noticed that use of [IrCl(coe)$_2$]$_2$ and [IrCl(cod)]$_2$ as a starting material can also yield the respective objective compounds in the same manner.

$^1$H NMR (CDCl$_3$, 35° C.): d; 6.6–8.4 (Aryl H of BINAP), −15.8 (br, hydride), −19.0 (br, hydride)

$^1$H NMR (CDCl$_3$, −10° C.): d; 6.6–8.4 (Aryl H of BINAP), −15.6 (t like, hydride), −19.0 (dd, hydride, J=7 Hz, 11 Hz)

$^{31}$P{$^1$H} NMR (CDCl$_3$, −10° C.): −4.6 (m), −12.8 (m)

IR (KBr): 2228 cm$^{-1}$ (br, Ir-H stretching)
ESI MS; m/z 2013 (M-I$^-$)
FAB MS; m/z 2013 (M-I$^-$)
Anal. Cacld For C$_{88}$H$_{66}$I$_4$Ir$_2$P$_4$: C, 49.40; H, 3.11; Found: C, 48.94; H, 2.90.
Mp: 110° C. (dec) Λ$_0$ (Electric conductivity)=180.2 Scm$^2$/mol

EXAMPLE 2

Synthesis of [{IrH((S)-BINAP)}$_2$(μ-Br)$_3$]Br

A 51.5 mg (0.0677 mmol) quantity of [IrBr(cod)]$_2$ and 5 mL of toluene were placed in a 20-mL Schlenk tube under an argon atmosphere, followed by stirring. To the resultant solution was added 88.5 mg (0.1421 mmol) of (S)-BINAP, followed by stirring at room temperature for 3 hours, and 39.4 μL (0.3385 mmol, 5.0 equivalents) of 47% hydroiodic acid was added to the reaction mixture, followed by stirring at room temperature overnight. The solvent was removed under reduced pressure, and the resultant residue was recrystallized from dichloromethane-hexane to give the subject title compound (125.0 mg, pale yellow solid). It meanwhile is to be noticed that use of [IrCl(coe)$_2$]$_2$ as a starting material can also yield the objective compound in the same manner.

$^1$H NMR (CDCl$_3$, 35° C.): d; 6.2-8.2 (Aryl H of BINAP), −21.52 (dd, J=14 Hz, 16 Hz, hydride),
$^{31}$P{$^1$H} NMR (CDCl$_3$, 35° C.): −0.9 (d, 19 Hz), −9.2 (d)
IR (KBr): 2268 cm$^{-1}$ (brs, Ir-H stretching)
ESI MS; m/z 1872 (M-Br$^-$)
FAB MS; m/z 1872 (M-Br$^-$)
Anal. Cacld for C$_{88}$H$_{66}$Br$_4$Ir$_2$P$_4$: C, 54.16; H, 3.41; Found: C, 53.63; H, 3.39.
Mp: 141° C. (dec)
Λ$_0$ (Electric conductivity)=139.78 Scm$^2$/mol

EXAMPLE 3

Synthesis of [{IrH((S)-BINAP)}$_2$(μ-Br)$_3$]Br

A 168.7 mg (0.2512 mmol) quantity of [IrCl(cod)]$_2$ and 5 mL of toluene were placed in a 20-mL Schlenk tube under an argon atmosphere, followed by stirring. To the resultant solution was added 326.3 mg (0.5240 mmol) of (S)-BINAP, followed by stirring at room temperature for 3 hours, and 143 μL (1.256 mmol, 5.0 equivalents) of 47% hydrobromic acid was added to the reaction mixture, followed by stirring at room temperature overnight. The solvent was removed under reduced pressure, and the resultant residue was recrystallized from dichloromethane-hexane to give the subject title compound (443.6 mg, pale yellow solid). NMR analysis and undetection of chlorine atom by EDAX supported that the resultant complex is the subject title complex free from chlorine.

EXAMPLE 4

Synthesis of [{IrH((S)-BINAP)}$_2$(μ-Cl)$_3$]Cl

A 120.0 mg (0.1790 mmol) quantity of [IrCl(cod)]$_2$ and 5 mL of toluene were placed in a 20-mL Schlenk tube under an argon atmosphere, followed by stirring. To the resultant solution was added 239.0 mg (0.3842 mmol) of (S)-BINAP, followed by stirring at room temperature for 3 hours, and 79.0 μL (0.90 mmol, 5.1 equivalents) of 35% hydrochloric acid was added to the reaction mixture, followed by stirring at room temperature overnight. The solvent was removed under reduced pressure, and the resultant residue was recrystallized from dichloromethane-hexane to give the subject title compound (290.7 mg, pale yellow solid).

$^1$H NMR (CDCl$_3$, 35° C.): d; 6.3-8.1 (Aryl H of BINAP), −22.70 (dd, J=6 Hz, 15 Hz, hydride), $^{31}$P{$^1$H} NMR (CDCl$_3$, 35° C.): −0.4 (d), −7.9 (d)

IR (KBr): 2269 cm$^{-1}$ (brs, Ir-H stretching)

FAB MS; m/z 1738 (M-Cl$^-$)

Anal. Cacld for C$_{88}$H$_{66}$Cl$_4$Ir$_2$P$_4$: C, 58.46; H, 3.62; Found: C, 58.51; H, 3.73.

Mp: 162° C. (dec)

$\Lambda_0$ (Electric conductivity)=301.60 Scm$^2$/mol

EXAMPLE 5

Synthesis of [{IrH((S)-BINAP)}$_2$(μ-I)$_3$]PF$_6$

A 62.9 mg (0.0294 mmol) quantity of [{IrH((S)-BINAP)}$_2$(μ-I)$_3$]I and 5 mL of THF were placed in a 20-mL Schlenk tube under an argon atmosphere, followed by stirring. To the resultant solution was added 112.0 mg (0.667 mmol) of NaPF$_6$, followed by stirring at room temperature overnight. The solvent was removed under reduced pressure to give the subject title compound (60.7 mg, yield of 96.5%).

$^1$H NMR (CDCl$_3$): d; 6.6-8.4 (Aryl H of BINAP), −19.0 (dd, hydride, J=7 Hz, 11 Hz), $^{31}$P{$^1$H} NMR (CDCl$_3$): −4.6 (dd like), −12.8 (dd like), −144.5 (sept, J$_{PF}$=706 Hz)

$^{19}$F NMR(CDCl$_3$): d; 77.0 (d, J$_{p-F}$=706 Hz)

IR (KBr): 2233 cm$^{-1}$ (br, Ir-H stretching)

EXAMPLE 6

Synthesis of [{IrH((S)-BINAP)}$_2$(μ-Br)$_3$]PF$_6$

A 64.8 mg (0.0332 mmol) quantity of [{IrH((S)-BINAP)}$_2$(μ-Br)$_3$]Br and 5 mL of THF were placed in a 20-mL Schlenk tube under an argon atmosphere, followed by stirring. To the resultant solution was added 112.0 mg (0.667 mmol) of NaPF$_6$, followed by stirring at room temperature overnight. The solvent was removed under reduced pressure to give the subject title compound (64.5 mg, yield of 96.4%).

$^1$H NMR (CDCl$_3$): d; 6.2-8.2 (Aryl H of BINAP), −21.52 (dd, J=14 Hz, 16 Hz, hydride), $^{31}$P{$^1$H} NMR (CDCl$_3$): −0.9 (d), −9.2 (d), −144.5 (sept, J$_{PF}$=706 Hz)

$^{19}$F NMR(CDCl$_3$): d; 77.0 (d, J$_{p-F}$=706 Hz)

IR (KBr): 2233 cm$^{-1}$ (br, Ir-H stretching)

EXAMPLE 7

Synthesis of [{IrH((S)-BINAP)}$_2$(μ-Cl)$_3$]PF$_6$

A 55.0 mg (0.0310 mmol) quantity of [{IrH((S)-BINAP)}$_2$(μ-Cl)$_3$]Cl and 5 mL of THF were placed in a 20-mL Schlenk tube under an argon atmosphere, followed by stirring. To the resultant solution was added 104.9 mg (0.625 mmol) of NaPF$_6$, followed by stirring at room temperature overnight. The solvent was removed under reduced pressure to give the subject title compound (51.7 mg, yield of 88.7%).

EXAMPLE 8

Synthesis of [{IrH((S)-BINAP)}$_2$(μ-I)$_3$]I

Ir(H)(I)((S)-BINAP)(CH$_3$CO$_2$) and toluene were placed in a 20-mL Schlenk tube under an argon atmosphere, followed by stirring. To the resultant solution was added 55% hydroiodic acid (10 equivalents for the iridium complex), followed by stirring at room temperature overnight. The solvent was removed under reduced pressure to give the subject title compound in yield of 90.9%.

EXAMPLES 9 TO 12

Asymmetric Hydrogenation for 6-phenyl-2,3,4,5-tetrahydropyridine

[{IrH((S)-BINAP)}$_2$(μ-X)$_3$]X (where X is the halogen atoms shown in Table 1), 6-phenyl-2,3,4,5-tetrahydropyridine (hereinafter referred to as briefly as "PhTHP") and toluene (in such a volume as was required to make the PhTHP concentration to 0.5 mol/L) were placed in a 100-mL autoclave, and the asymmetric hydrogenation was carried out at 20° C., under the hydrogen pressure of 6 MPa, for 3 hours. The obtained results are presented in Table 1.

[Analysis of the Reaction Conversion Ratio]

Measurement was made by GLC with use of a capillary column DB-1 (manufactured by J & W Scientific Co.).

[Determination of Optical Purity]

The resultant amine was trifluoroacetamidated, followed by determination of the optical purity by GLC with use of a capillary column Chrasil-DEX CB (manufactured by Chrompack Co.).

TABLE 1

| Example | X | S/C | Conversion (%) | Enantiomeric excess(ee %) | Absolute configuration |
|---|---|---|---|---|---|
| 9 | I | 1000 | >99 | 91 | S |
| 10 | I | 4000 | 79 | 90 | S |
| 11 | Br | 1000 | 97 | 90 | S |
| 12 | Cl | 1000 | 78 | 89 | S |

Remarks: "S/C" denotes a molar ratio of PhTHP/Ir complex.

INDUSTRIAL APPLICABILITY

The iridium complexes as defined in the present invention, when used as a catalyst, permit the highly stereoselective reactions to be carried out, thus producing optically active compounds in high yields. In addition, such optically active compounds are useful as an intermediate for synthesis of various compounds.

The invention claimed is:

1. An iridium complex represented by the formula(1):

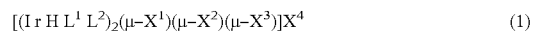

wherein L$^1$ and L$^2$ may be the same or different and each represent a monodendate neutral ligand, or each cooperate with the other to form a bidendate neutral ligand; X$^1$, X$^2$ and X$^3$ may be the same or different, and each represent a halogen atom; and X$^4$ is a counter-anion, and wherein the monodendate neutral ligand or bidendate neutral ligand is optically active.

2. The iridium complex according to claim 1, wherein the monodendate neutral ligand is a phosphine compound, an oxazoline or a nitrogen-containing heterocyclic carbene.

3. The iridium complex according to claim 2, wherein the phosphine compound is a trialkylphosphine, triarylphosphine or dialkylarylphosphine.

4. The iridium complex according to claim 2, wherein the oxazoline is a compound represented by the formula (2):

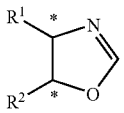

(2)

wherein $R^1$ and $R^2$ may be the same or different and each represent an alkyl, aryl or heteroaryl group; and two of the symbol "*" represent a chiral or non-chiral carbon atom.

5. The iridium complex according to claim 2, wherein the nitrogen-containing heterocyclic carbene is a compound selected from the group consisting of:

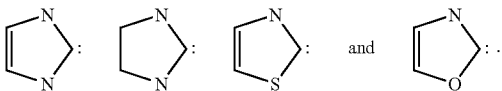

6. The iridium complex according to claim 1, wherein the bidendate neutral ligand is a bisphosphine, a diamine, a bisoxazoline or a biscarbene.

7. The iridium complex according to claim 6, wherein the bisphosphine is a compound represented by the formula (3):

wherein $R^3$, $R^4$, $R^5$ and $R^6$ each independently represent an alkyl, aryl or heterocyclic group; and $Q^1$ is a divalent group.

8. The iridium complex according to claim 6, wherein the diamine is a compound represented by the formula (4):

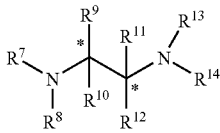

(4)

wherein $R^7$, $R^8$, $R^{13}$ and $R^{14}$ may be the same or different, and each represent a hydrogen atom or an alkoxycarbonyl or sulfonyl group; $R^9$, $R^{10}$, $R^{11}$ and $R^{12}$ may be the same or different, and each represent a hydrogen atom, an alkyl or monocyclic or polycyclic aromatic hydrocarbon group; $R^9$ and $R^{11}$, or $R^{10}$ and $R^{12}$ may combine with each other, respectively, to form a ring; and the symbol "*" is a chiral or non-chiral carbon atom.

9. The iridium complex according to claim 6, wherein the bisoxazoline is a compound represented by the formula (5):

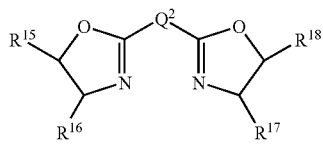

(5)

wherein $R^{15}$, $R^{16}$, $R^{17}$ and $R^{18}$ each are a hydrogen atom (provided, that $R^{15}$ and $R^{16}$ are not a hydrogen atom at the same time, and that $R^{17}$ and $R^{18}$ are not a hydrogen atom at the same time), a phenyl group which may be substituted with an alkyl group of 1 to 6 carbon atoms, an alkoxy group of 1 to 6 carbon atoms or a halogen atom, or a benzyl group which may be substituted with an alkyl group(s) of 1 to 6 carbon atoms, an alkoxy group of 1 to 6 carbon atoms or a halogen atom; $Q^2$ is a phenylene, biphenyldiyl or binaphthalenediyl group, whereby the biphenyldiyl or naphthalenediyl group may have axial chirality.

10. The iridium complex according to claim 6, wherein the biscarbene is a compound represented by the formula (6):

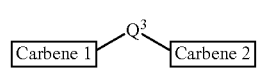

(6)

wherein $Q^3$ is an alkylene, phenylene, biphenyldiyl or binaphthalenediyl group, whereby the alkylene group may have a chiral carbon atom and the biphenylenediyl or binaphthalenediyl group may have the axial chirality; and the carbene 1 and carbene 2 may be the same or different, and each represent a nitrogen-containing heterocyclic carbene.

11. A catalyst, wherein the catalyst comprises the iridium complex according to claim 1.

12. The catalyst according to claim 11, wherein the catalyst is used in asymmetric hydrogenation.

* * * * *